(12) United States Patent
Shelchuk et al.

(10) Patent No.: US 7,848,793 B1
(45) Date of Patent: Dec. 7, 2010

(54) MONITORING FOR MITRAL VALVE REGURGITATION

(75) Inventors: Anne M. Shelchuk, Cupertino, CA (US); Michael Paris, San Francisco, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 762 days.

(21) Appl. No.: 11/537,322

(22) Filed: Sep. 29, 2006

(51) Int. Cl.
*A61B 5/04* (2006.01)

(52) U.S. Cl. ..................................... 600/509
(58) Field of Classification Search ................. 600/509, 600/513, 508; 607/18, 23
See application file for complete search history.

(56) References Cited

U.S. PATENT DOCUMENTS

| | | | |
|---|---|---|---|
| 4,712,555 A | 12/1987 | Thornander et al. | |
| 4,788,980 A | 12/1988 | Mann et al. | |
| 4,940,052 A | 7/1990 | Mann et al. | |
| 4,944,298 A | 7/1990 | Sholder | |
| 5,466,254 A | 11/1995 | Helland | |
| 5,476,483 A | 12/1995 | Bornzin et al. | |
| 6,128,534 A | 10/2000 | Park et al. | |
| 6,480,733 B1 | 11/2002 | Turcott | |
| 6,512,952 B2 | 1/2003 | Stahmann et al. | |
| 6,512,953 B2 | 1/2003 | Florio et al. | |
| 6,527,729 B1 | 3/2003 | Turcott | |
| 6,572,557 B2 | 6/2003 | Tchou et al. | |
| 6,610,018 B1 | 8/2003 | McIntyre | |
| 6,622,045 B2 | 9/2003 | Snell et al. | |
| 6,628,988 B2 | 9/2003 | Kramer et al. | |
| 6,643,546 B2 | 11/2003 | Mathis et al. | |
| 6,643,548 B1 | 11/2003 | Mai et al. | |
| 6,658,292 B2 | 12/2003 | Kroll et al. | |
| 6,666,826 B2 | 12/2003 | Salo et al. | |
| 6,741,885 B1 | 5/2004 | Park et al. | |
| 6,792,308 B2 * | 9/2004 | Corbucci | ..................... 607/17 |
| 6,832,113 B2 | 12/2004 | Belalcazar | |
| 6,915,162 B2 | 7/2005 | Noren et al. | |
| 6,922,587 B2 | 7/2005 | Weinberg | |
| 6,934,586 B2 | 8/2005 | Struble et al. | |
| 6,942,622 B1 | 9/2005 | Turcott | |
| 6,970,742 B2 | 11/2005 | Mann et al. | |

(Continued)

FOREIGN PATENT DOCUMENTS

WO     2003089056 A1    10/2003

(Continued)

OTHER PUBLICATIONS

Klabunde, Richard E., "Cardiac Function", Chapter 4 (pp. 59-90) of book entitled Cardiovascular Physiological Concepts, Published by Lippincott Williams & Wilkins, 2004.

*Primary Examiner*—Mark W Bockelman
*Assistant Examiner*—Roland Dinga
(74) *Attorney, Agent, or Firm*—Steven M. Mitchell

(57) ABSTRACT

Implantable systems, and methods for use therein, for monitoring for mitral valve regurgitation (MR) are provided. An electrogram (EGM) signal and a corresponding pressure signal are obtained, where the EGM signal is representative of electrical functioning of the patient's heart during a plurality of cardiac cycles, and the corresponding pressure signal is representative of pressure within the left atrium the patient's heart during the cardiac cycles. Windows of the pressure signal are defined, based on events detected in the EGM signal, and measurements from the windows are used to monitor for MR.

6 Claims, 9 Drawing Sheets

U.S. PATENT DOCUMENTS

| | | | |
|---|---|---|---|
| 7,013,734 B2 | 3/2006 | Zdeblick et al. | |
| 7,028,550 B2 | 4/2006 | Zdeblick et al. | |
| 7,066,031 B2 | 6/2006 | Zdeblick et al. | |
| 7,073,387 B2 | 7/2006 | Zdeblick et al. | |
| 7,082,330 B2 * | 7/2006 | Stadler et al. | 607/17 |
| 7,437,192 B2 * | 10/2008 | Gill et al. | 607/23 |
| 7,450,999 B1 * | 11/2008 | Karicherla et al. | 607/126 |
| 7,526,338 B1 * | 4/2009 | Gill et al. | 607/18 |
| 2002/0058969 A1 * | 5/2002 | Noren et al. | 607/17 |
| 2003/0055345 A1 | 3/2003 | Eigler et al. | |
| 2003/0199934 A1 | 10/2003 | Struble et al. | |
| 2004/0106874 A1 | 6/2004 | Eigler et al. | |
| 2004/0167580 A1 * | 8/2004 | Mann et al. | 607/17 |
| 2004/0172077 A1 | 9/2004 | Chinchoy | |
| 2005/0160823 A1 | 7/2005 | Zdeblick et al. | |
| 2005/0160824 A1 | 7/2005 | Zdeblick et al. | |
| 2005/0160825 A1 | 7/2005 | Zdeblick et al. | |
| 2005/0160826 A1 | 7/2005 | Zdeblick et al. | |
| 2005/0288722 A1 | 12/2005 | Eigler et al. | |
| 2006/0009810 A1 | 1/2006 | Mann et al. | |
| 2006/0137457 A1 | 6/2006 | Zdeblick et al. | |
| 2006/0149155 A1 | 7/2006 | Hedberg | |
| 2006/0149331 A1 | 7/2006 | Mann et al. | |
| 2006/0224204 A1 * | 10/2006 | Hettrick et al. | 607/23 |

FOREIGN PATENT DOCUMENTS

| | | |
|---|---|---|
| WO | 2004078254 A2 | 9/2004 |
| WO | 2005058133 | 6/2005 |
| WO | 2005058133 A2 | 6/2005 |
| WO | 2005058133 A3 | 6/2005 |

* cited by examiner

MONITORING FOR MITRAL VALVE REGURGITATION

RELATED APPLICATION

The present application relates to commonly invented and commonly assigned U.S. patent application Ser. No. 11/537,302, entitled "Estimating Mean Left Atrial Pressure," which was filed the same day as the present application, and which is incorporated herein by reference.

FIELD OF THE INVENTION

Embodiments of present invention relate to monitoring for mitral valve regurgitation (MR).

BACKGROUND

Heart failure is a condition in which a patient's heart works less efficiently than it should, resulting in the heart failing to supply the body sufficiently with the oxygen rich blood it requires, either at exercise or at rest. Congestive heart failure (CHF) is heart failure accompanied by a build-up of fluid pressure in the pulmonary blood vessels that perfuse the lungs. Transudation of fluid from the pulmonary veins into the pulmonary interstitial spaces, and eventually into the alveolar air spaces, is called pulmonary edema, and can cause shortness of breath, hypoxia, acidosis, respiratory arrest, and even death.

Chronic diseases such as CHF require close medical management to reduce morbidity and mortality. Because the disease status evolves with time, frequent physician follow-up examinations are typically necessary. At follow-up, the physician may make adjustments to the drug regimen in order to optimize therapy. This conventional approach of periodic follow-up is unsatisfactory for some diseases, such as CHF, in which acute, life-threatening exacerbations can develop between physician follow-up examinations. It is well know among clinicians that if a developing exacerbation is recognized early, it can be more easily and inexpensively terminated, typically with a modest increase in oral diuretic. However, if it develops beyond the initial phase, an acute heart failure exacerbation becomes difficult to control and terminate. Hospitalization in an intensive care unit is often required. It is during an acute exacerbation of heart failure that many patients succumb to the disease.

It is often difficult for patients to subjectively recognize a developing exacerbation, despite the presence of numerous physical signs that would allow a physician to readily detect it. Furthermore, since exacerbations typically develop over hours to days, even frequently scheduled routine follow-up with a physician cannot effectively detect most developing exacerbations. It is therefore desirable to have a system that allows for routine, frequent monitoring of patients so that an exacerbation can be recognized early in its course. With the patient and/or physician thus notified by the monitoring system of the need for medical intervention, a developing exacerbation can more easily and inexpensively be terminated early in its course.

Mitral valve regurgitation (MR) is a condition in which the mitral valve doesn't close tightly, which allows blood to flow backward in a patient's heart. When the mitral valve doesn't function properly, blood can't move through the heart or to the rest of the patient's body as efficiently. The condition can leave a patient fatigued and short of breath. As many as one in five people over age 55 have some degree of MR. Treatment of MR depends on the severity and progression of the condition and signs and symptoms. A patient may need heart surgery to repair or replace the valve. Left unchecked, severe MR can lead to CHF or serious heart rhythm irregularities (i.e., arrhythmias). MR is also called mitral insufficiency, mitral incompetence or simply mitral regurgitation.

Accordingly, it would be advantageous to provide implantable cardiac devices that can obtain information about a patient's heart failure progression and information about occurrences of MR. More generally, it is desirable to provide implantable cardiac devices that can obtain disease progression information.

SUMMARY

Certain embodiments of the present invention relate to implantable systems, and method for use therein, for monitoring a patient's heart for MR. In accordance with specific embodiments of the present invention, an EGM signal and a corresponding pressure signal are obtained, where the EGM signal is representative of electrical functioning of the patient's heart during a plurality of cardiac cycles, and the corresponding pressure signal is representative of pressure within the left atrium of the patient's heart during the cardiac cycles. In accordance with specific embodiments, for each of a plurality of cardiac cycles represented in the EGM and pressure signals, there is a determination of a maximum peak within a first window of the pressure signal, and a determination of a maximum peak within a second window of the pressure signal. The maximum peak detected within one or more first window is compared to the maximum peak detected within one or more second window. MR is monitored for based on results of the comparison.

In accordance with specific embodiments, a start of the first window is defined relative to an event detected in the EGM signal, and a length of the first window is defined to include at least one of an a-wave and a c-wave, but not a v-wave, of the cardiac cycle represented in the pressure signal. In accordance with certain embodiments, a start of the second window is defined relative to an event detected in the EGM signal or relative to the first window, and a length of the second window is defined to include the v-wave of the cardiac cycle represented in the pressure signal.

In accordance with other embodiments, for each of a plurality of cardiac cycles represented in the EGM and pressure signals, there is a determination of a maximum peak within a first window of the pressure signal, there is a determination of an average of a first window of the pressure signal, and a determination of an average of a second window of the pressure signal. One or more average determined for a first window is compared to one or more average determined for a second window, and MR is monitored based on results of the comparison.

This description is not intended to be a complete description of, or limit the scope of, the invention. Additional and alternative features, aspects, and objects of the invention can be obtained from a review of the specification, the figures, and the claims.

Figure 1A:
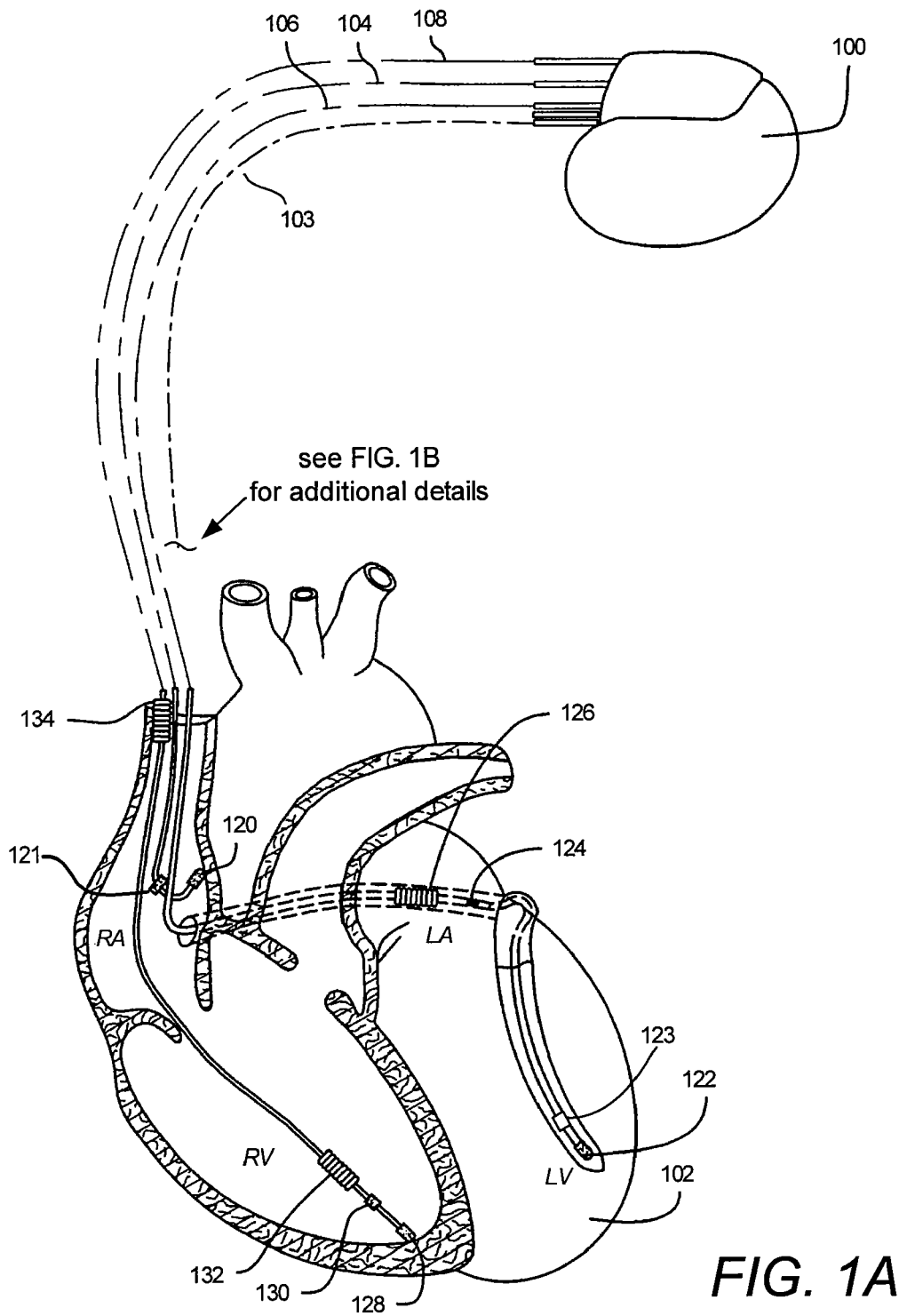
FIG. 1A is a simplified diagram illustrating an exemplary implantable device in electrical communication with a patient's heart by means of multiple leads suitable for delivering multi-chamber stimulation and pacing therapy.

In accordance with common practice the various features illustrated in the drawings may not be drawn to scale. Accordingly, the dimensions of the various features may be arbitrarily expanded or reduced for clarity. In addition, some of the drawings may be simplified for clarity. Thus, the drawings may not depict all of the components of a given apparatus or method. Finally, like reference numerals denote like features throughout the specification and figures.

DETAILED DESCRIPTION

The following detailed description of the present invention refers to the accompanying drawings that illustrate exemplary embodiments consistent with this invention. Other embodiments are possible, and modifications may be made to the embodiments within the spirit and scope of the present invention. Therefore, the following detailed description is not meant to limit the invention. Rather, the scope of the invention is defined by the appended claims.

It would be apparent to one of skill in the art that the present invention, as described below, may be implemented in many different embodiments of hardware, software, firmware, and/or the entities illustrated in the figures. Any actual software and/or hardware described herein is not limiting of the present invention. Thus, the operation and behavior of the present invention will be described with the understanding that modifications and variations of the embodiments are possible, given the level of detail presented herein.

It is believed that chronic monitoring of the pressures within the chambers of the heart will be important in future cardiac pulse generator applications. To monitor congestive heart failure (CHF) status, clinicians ideally would like to know left ventricular end-diastolic pressure (LVEDP). However, it is rarely possible to directly measure LVEDP because of the invasiveness required of a transducer capable of making such a measurement. An alternative is to measure left atrial pressure (LAP) at a time when the pressure in the left atrium and left ventricle is the same, namely at the end of an atrial contraction, when the mitral valve (located between the left and right atrium) is still open. This is the end of ventricular diastole. The most clinically-relevant time then to report LAP is in this interval. Accordingly, there is a desire to provide relatively accurate and efficient systems and methods for measuring LAP. Such LAP measurements can then be used as an estimate or surrogate for LVEDP, in certain embodiments of the present invention.

Before describing embodiments of the invention in additional detail, it is helpful to first describe an example environment in which embodiments of the invention may be implemented.

Figure 1B:
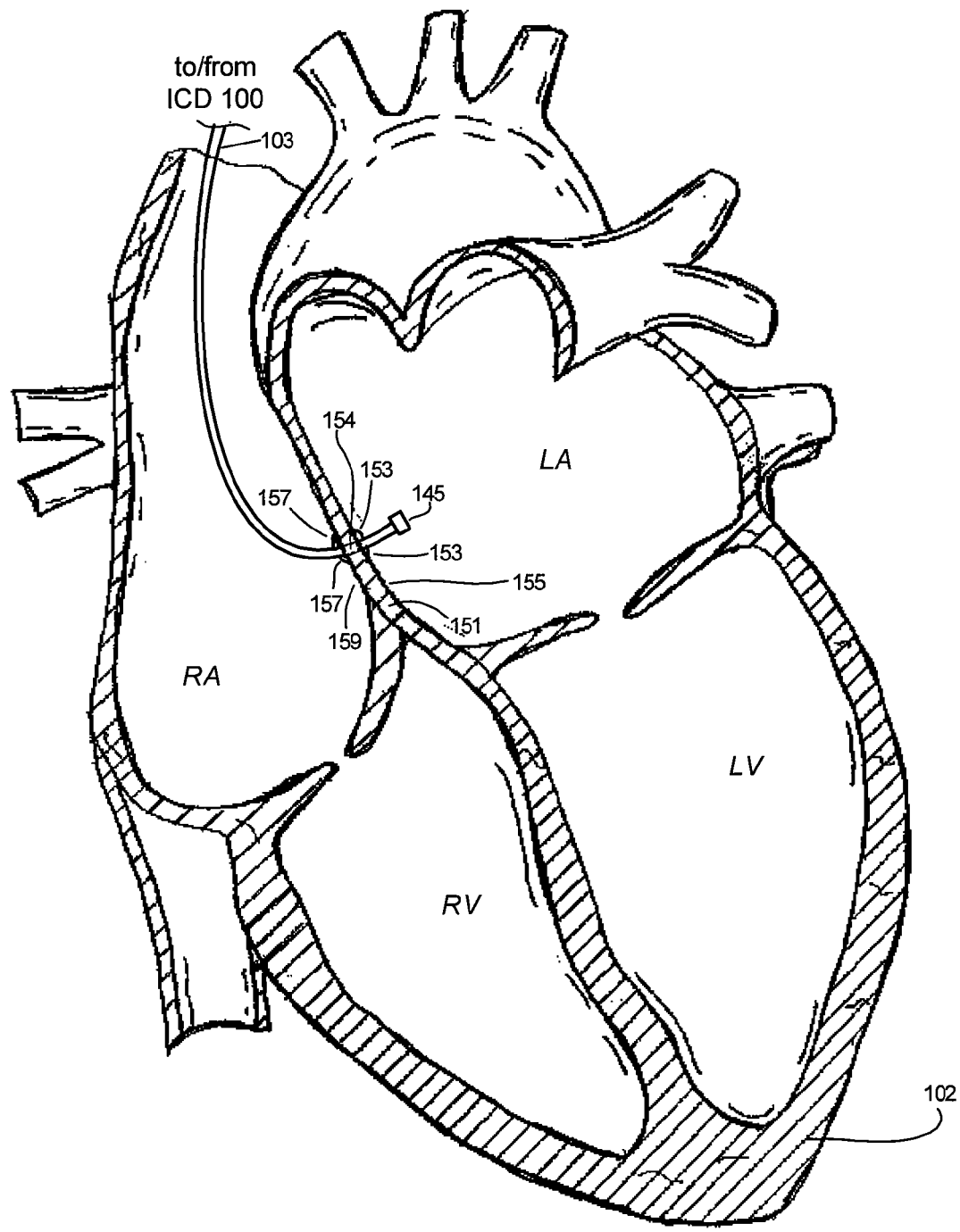
FIG. 1B is useful for describing how pressure sensors can be implanted within a patient's heart and connected by leads to the implantable device of FIG. 1A.
Figure 2:
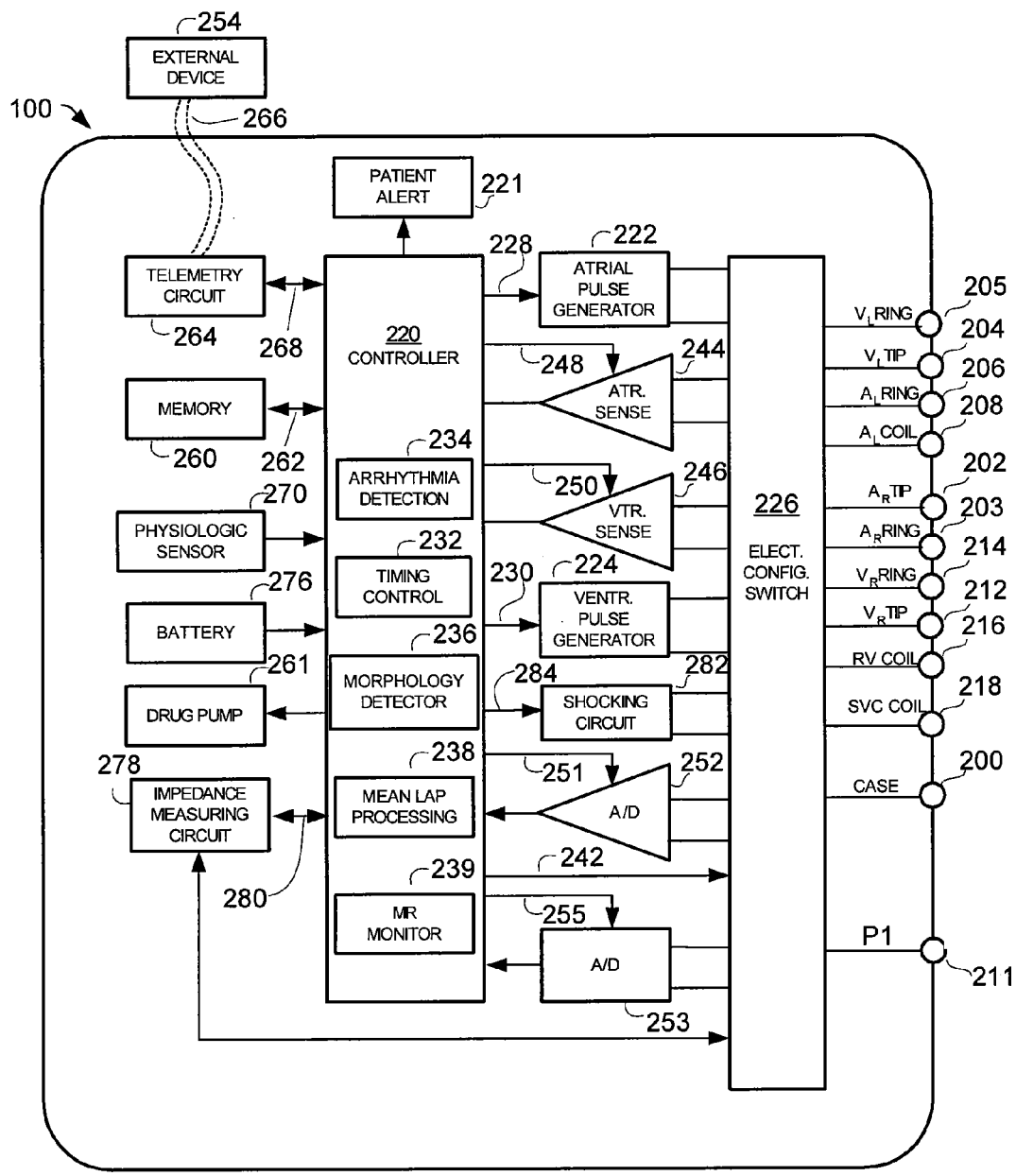
FIG. 2 is a functional block diagram of the exemplary implantable device, which can provide cardioversion, defibrillation, and pacing stimulation in four chambers of a heart, and can estimate mean LAP and/or detect MR, in accordance with embodiments of the present invention.

Embodiments of the present invention are particularly useful in the environment of an implantable cardiac device that may monitor electrical activity of a heart and deliver appropriate electrical therapy, including for example, pacing pulses, cardioverting and defibrillator pulses, and/or drug therapy, as required. Implantable cardiac devices include, for example, pacemakers, cardioverters, defibrillators, implantable cardioverter defibrillators, and the like. The term "implantable cardiac device" or simply "ICD" is used herein to refer to any implantable cardiac device, even those that don't deliver electrical stimulation (e.g., the implantable device may simply be a monitor that records data). FIGS. 1A and 2, discussed below, illustrate such an environment in which embodiments of the present invention can be used. FIG. 1B, which is useful for describing how pressure sensors can be implanted within a patient's heart and connected by leads to the implantable device of FIG. 1A, is also discussed below.

Referring first to FIG. 1A, an exemplary implantable device 100 is shown as being in electrical communication with a patient's heart 102 by way of three leads 104, 106, and 108, suitable for delivering multi-chamber stimulation and shock therapy. To sense atrial cardiac signals and to provide right atrial chamber stimulation therapy, implantable device 100 is coupled to an implantable right atrial lead 104 having at least an atrial tip electrode 120, which typically is implanted in the patient's right atrial appendage or septum. FIG. 1A shows the right atrial lead 104 also as having an optional atrial ring electrode 121.

To sense left atrial and ventricular cardiac signals and to provide left chamber pacing therapy, implantable device 100 is coupled to a coronary sinus lead 106 designed for placement in the coronary sinus region via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 106 is designed to receive atrial and ventricular cardiac signals and to deliver left ventricular pacing therapy using at least a left ventricular tip electrode 122, left ventricular ring electrode 123, left atrial pacing therapy using at least a left atrial ring electrode 124, and shocking therapy using at least a left atrial coil electrode 126 (or other electrode capable of delivering a shock). For a more complete description of a coronary sinus lead, the reader is directed to U.S. Pat. No. 5,466,254, "Coronary Sinus Lead with Atrial Sensing Capability" (Helland), which is incorporated herein by reference.

Implantable device 100 is also shown in electrical communication with the patient's heart 102 by way of an implantable right ventricular lead 108 having, in this implementation, a right ventricular (RV) tip electrode 128, a right ventricular ring electrode 130, a right ventricular coil electrode 132 (or other electrode capable of delivering a shock), and superior vena cava (SVC) coil electrode 134 (or other electrode capable of delivering a shock). Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle.

Also shown in FIG. 1A is a lead 103 to which is attached a pressure sensor, not shown in FIG. 1A, but shown in FIG. 1B (which is a cutaway view of the heart 102 from a different angle than shown in FIG. 1B). Referring now to FIG. 1B, the lead 103 includes a pressure sensor 145 located in the left atrium (LA). In this embodiment, the distal tip of the lead 103 contains the left atrial pressure sensor 145. As will be described below, the implantable device 100 includes circuitry that processes signals from the sensor 145 to estimate mean left atrial pressure (LAP) and/or monitor for mitral valve regurgitation (MR), in accordance with embodiments of the present invention.

To pass the lead 103 through to the left atrium (LA), the atrial septal wall 151 may be pierced using, for example, a piercing guide wire tool (not shown), or using a lead 103 that includes on its distal end a relatively sharp and hard tip (not shown), or using a lead that includes a deployable and retractable piercing mechanism. The piercing apparatus is manipulated to create an access tunnel 154 in the septum 151. The access tunnel 154 may be made in the region of the fossa ovalis since this may be the thinnest portion of the atrial septum 151.

The distal portion of the lead 103 is then maneuvered through the atrial septum 151 (e.g., using the stylet) so that all or a portion of the pressure sensor 145 at the distal end of the lead 103 protrudes into the left atrium. In this way, the sensor 145 may be used to accurately measure pressure in the left atrium. If desired, the lead 103 also may include another pressure sensor (not shown) positioned proximally on the lead from the sensor 145, to thereby measure pressure in the right atrium (RA).

The lead 103 can include an attachment structure that serves to attach the lead 103 to the septum 151. The attachment structure may take many forms including, without limitation, one or more tines, flexible membranes, inflatable membranes, circumferential tines and/or J-leads. FIG. 1B represents the attachment structure in a generalized manner.

In the embodiment of FIG. 1B, the attachment structure includes a first attachment structure 153 and a second attachment structure 157 implanted on opposite sides of the septum 151. In other applications a single attachment structure may be implanted on one of the sides of the septum 151.

In accordance with an embodiment, the first attachment structure 153 is attached to the distal portion of the lead 103. After the first attachment structure 153 is pushed through an access tunnel 154 pierced through the septum 151, it expands outwardly from the lead 103 such that it tends to prevent the distal end of the lead 103 from being pulled back through the access tunnel 154. The first attachment structure 153 is then positioned against a septal wall 155 in the left atrium.

The second attachment structure 157 extends outwardly from the lead 103 to help prevent the lead 103 from sliding further down into the left atrium. As FIG. 1B illustrates, the second attachment structure 157 is positioned against a septal wall 159 in the right atrium.

In some embodiments the attachment structures 153 and 157 are positioned a pre-defined distance apart on the lead 103. For example, the lead may be constructed so that the spacing between the attachment structures 153 and 157 is approximately equal to the thickness of the septum 151 in the area of the access tunnel 154. In some embodiments the attachment structures are retractable to facilitate subsequent lead extraction.

In some embodiments, one or more of the attachment structures 153 and 157 are attached to the lead 103 in a manner that enables the position of the attachment structure to be adjusted. For example, one or both of the attachment structures 153 and 157 may be slideably mounted to the lead 103 so that they may be moved toward one another to firmly place each attachment structure against the septum 151. Such movement of the attachment structures 153 and 157 may be accomplished, for example, by a manual operation (e.g., via a tensile member such as a stylet or a sheath) or automatically through the use of a biasing member (e.g., a spring).

The attachment structures are preferably configured so that they have a relatively low profile against the septal wall 151. In this way, problems associated with protruding objects in the side of the heart may be avoided. For example, it is possible that blood clots may form on an object that protrudes from a wall of the heart. If these blood clots break loose in the left side of the heart the blood clots may travel to other areas of the body such as the brain and cause a blockage in a blood vessel (i.e., an embolism). By configuring the attachment(s) to have a low profile, a biological layer of endothelial cells ("the intima") may quickly build up over the attachment structure. As a result, the likelihood of blood clots breaking loose may be significantly reduced. The buildup of the intima also may assist in firmly attaching the attachment structure(s) 153 and/or 157 to the septal wall 151. As a result, the lead 103 may be attached to the heart in a sufficiently stable manner so as to prevent injury to the heart and provide accurate pressure measurements.

Various control apparatus may be attached to the proximal end of the lead 103. For example, mechanisms may be provided for moving stylets or guide wires, movable sheaths or other components (not shown) in the lead 103 or for controlling the flow of fluid through lumens in the lead 103. In some applications, the control apparatus may be removed from the lead 103 when the device 100 (not shown in FIG. 1B) attached to proximal end of the lead is implanted in the patient.

In other embodiments, the pressure sensor 145 can be attached to one of the same leads that is used for measuring electrical activity and/or delivering electrical stimulation to the left atrium of the heart. For example, the left atrial pressure sensor 145 can be connected to the portion of the coronary sinus lead 106 (shown in FIG. 1A) that is located in the left atrium.

The pressure sensor 145 can be an analog device that produces an analog signal, or a digital device that produces a digital signal. An example of an ultra small digital pressure sensor is the SM5201 from Silicon Microstructures Incorporated (SMI) in Milpitas, Calif. An example of an ultra small analog pressure sensor is the SM5112 from Silicon Microstructures Incorporated (SMI) in Milpitas, Calif. It is also possible that a hollow lumen catheter can be inserted within the left atrium, with the hollow lumen catheter being in communication with a pressure transducer located within the housing of the implantable device 100. In such an embodiment, it will still be stated that the pressure sensor is located within a chamber of the heart since the hollow lumen can be considered part of the sensor. These are just a few examples, which are not meant to be limiting. Other pressure sensors can be used.

The lead 103 can include a lead body that may house one or more electrical conductors, fluid-carrying lumens and/or other components (not shown). For example, the lead 103 to which the pressure sensor 145 is attached may include three conductors, one for providing an excitation voltage required to power the sensor 145, one for ground, one to carry the analog or digital pressure signal produced by the sensor 145.

The lead 103 could be connected to a device header with, e.g., an IS-1 or IS-4 connector assembly. The implanted device could then process the left atrial pressure signal and make various calculations based from the signal provided.

It is noted that measurements made by the implanted pressure sensor 145 may be affected by changes in ambient pressure that result, e.g., from changes in weather and/or altitude. For a more specific example, when a person having the implanted pressure sensor 145 drives up a mountain, or ascends in an airplane, measurements from the implanted pressure sensor 145 may indicate an decrease in pressure. Such confounding factors may affect the ability of the implanted system to estimate mean LAP, since the measured change in pressure is not due to physiologic changes. One way to overcome this problem is for the person to carry an external device that monitors ambient pressure, which can be used to calibrate/adjust the endocardial pressure measurements. For example, the external device (not shown) can wirelessly transmit the ambient pressure measurements to the implanted system 100, which can then appropriately calibrate/adjust the endocardial pressure measurements. In another embodiment, there is calibration pressure sensor located within or attached to the implantable device or within another chamber of the heart, which is used to calibrate/adjust pressure measurements from sensor 145.

While specific techniques for implanting pressure sensors have been described above, this was merely for completeness. Embodiments of the present invention can be used with all techniques for placement of pressure sensors.

Through the use of the above described lead and sensor, and, in some cases, other leads and sensors implanted in the patient, the implantable cardiac device 100 can be used to estimate mean LAP and/or monitor for MR, in accordance with embodiments of the present invention, as will be described below. However, before going into more details about how embodiments of the present invention estimate mean LAP and/or monitor for MR, additional details of the exemplary implantable device 100 will be discussed in conjunction with FIG. 2.

FIG. 2 shows a simplified block diagram depicting various components of the exemplary implantable device 100. The implantable device 100, as shown, can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the techniques and methods described below can be implemented in connection with any suitably configured or configurable implantable device. Accordingly, one of skill in the art could readily duplicate, eliminate, or disable the appropriate circuitry in any desired combination.

A housing 200 for the implantable device 100 is often referred to as the "can", "case" or "case electrode", and may be programmably selected to act as the return electrode for all "unipolar" modes. The housing 200 may further be used as a return electrode alone or in combination with one or more of the coil electrodes 126, 132 and 134 for shocking purposes. The housing 200 further includes a connector (not shown) having a plurality of terminals 202, 204, 206, 208, 212, 214, 216, and 218 (shown schematically and, for convenience, the names of the electrodes to which they are connected are shown next to the terminals).

To achieve right atrial sensing and pacing, the connector includes at least a right atrial tip terminal (AR TIP) 202 adapted for connection to the atrial tip electrode 120. A right atrial ring terminal (AR RING) 203 may also be included adapted for connection to the atrial ring electrode 121. To achieve left chamber sensing, pacing, and shocking, the connector includes at least a left ventricular tip terminal (VL TIP) 204, left ventricular ring terminal (VL RING) 205, a left atrial ring terminal (AL RING) 206, and a left atrial shocking terminal (AL COIL) 208, which are adapted for connection to the left ventricular tip electrode 122, the left atrial ring electrode 124, and the left atrial coil electrode 126, respectively.

To support right chamber sensing, pacing, and shocking, the connector further includes a right ventricular tip terminal (VR TIP) 212, a right ventricular ring terminal (VR RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

At the core of the implantable device 100 is a programmable microcontroller 220 that controls the various modes of stimulation therapy. As is well known in the art, microcontroller 220 typically includes one or more microprocessors, or equivalent control circuitry, designed specifically for controlling the delivery of stimulation therapy, and may further include RAM or ROM memory, logic and timing circuitry, state machine circuitry, and/or I/O circuitry. Typically, microcontroller 220 includes the ability to process and/or monitor input signals (data or information) as controlled by a program code stored in a designated block of memory (e.g., memory 260). The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals used within the implantable device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart, the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 can also include timing control circuitry 232 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module, the latter two are not shown in FIG. 2. These components can be utilized by the implantable device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured (e.g., via signal line 251) to acquire intracardiac electrogram ("IEGM") signals, convert the raw analog data into a digital signal, and can store the digital signals for later processing and/or telemetric transmission to an external device 254. The data acquisition system 252 can be coupled to the right atrial lead 104, the coronary sinus lead 106, and the right ventricular lead 108 through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the implantable device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device. The memory 260 can also store the pressure data related to embodiments of the present invention.

The operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The implantable device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output, changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses. While shown as being included within the implantable device 100, it is to be understood that the physiologic sensor 270 may also be external to the implantable device 100, yet still be implanted within or carried by the patient. Examples of physiologic sensors that may be implemented in device 100 include known sensors that, for example, sense respiration rate, pH of blood, ventricular gradient, oxygen saturation, blood pressure and so forth. Another sensor that may be used is one that detects activity variance, wherein an activity sensor is monitored diurnally to detect the low variance in the measurement corresponding to the sleep state. For a more detailed description of an activity variance sensor, the reader is directed to U.S. Pat. No. 5,476,483 (Bornzin et al.), which is hereby incorporated by reference.

The implantable device 100 additionally includes a battery 276 that provides operating power to all of the circuits shown in FIG. 2. For a device that employs shocking therapy, the battery 276 should be capable of operating at low current drains for long periods of time (e.g., preferably less than 10 μA), and be capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The implantable device 100 can further include magnet detection circuitry (not shown), coupled to the microcontroller 220, to detect when a magnet is placed over the implantable device 100. A magnet may be used by a clinician to perform various test functions of the implantable device 100 and/or to signal the microcontroller 220 that the external programmer 254 is in place to receive or transmit data to the microcontroller 220 through the telemetry circuits 264.

The exemplary implantable device 100 is also shown as including an impedance measuring circuit 278 that is enabled by the microcontroller 220 via a control signal 280. The known uses for an impedance measuring circuit 278 include, but are not limited to, lead impedance surveillance during the acute and chronic phases for proper performance; lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the implantable device 100 is intended to operate as an implantable cardioverter/defibrillator device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J to 2.0 J), moderate (e.g., 2.5 J to 10 J), or high energy (e.g., 11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, and/or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

A typical pressure sensor generates electrical signals indicative of changes in a sensed pressure. Thus, one or more wires may be used to connect the sensor 145 to the device 100, as was described above. FIG. 2 illustrates an embodiment where a pressure signal P1 (e.g., from sensor 145) is received by the device 100 via terminal 211. An analog-to-digital (ND) data acquisition system 253 may be configured (e.g., via signal line 255) to acquire and amplify the signal P1, convert the raw analog data into a digital signal, filter the signal and store the digital signal (e.g., in memory 260) for later processing by, for example, a mean LAP processing component 238, a MR monitoring component 239 and/or telemetric transmission to an external device 254. As mentioned above, it is also possible that the pressure sensor can produce a digital signal. In such a case, the ND 253 would not be needed. In addition to (or instead of) storing the pressure signals, it is also possible that the pressure signals be processing in real or near real time.

The implanted device 100 is also shown as including a patient alert 221, which can inform the patient that medical attention should be sought. In accordance with an embodiment, the alert 221 is provided through an electromechanical transducer that generates sound and/or mechanical vibration, that can be heard and/or felt by the patient. These are just a few examples of patient alerts, which are not meant to be limiting. One of ordinary skill in the art will appreciate that other types of patient alerts can be used, while still being within the spirit and scope of the present invention.

The implantable device may also includes a drug pump 261, controlled by the microcontroller 220, to compensate, if necessary, for drug efficacy problems. For example, if an initial dosage of a drug for treating CHF is not adequately effective, the drug pump may be controlled to increase the dosage.

Now that exemplary details of the implantable device 100 have been provided, additional details of the various embodiments of the present invention will be provided.

Figure 3A:
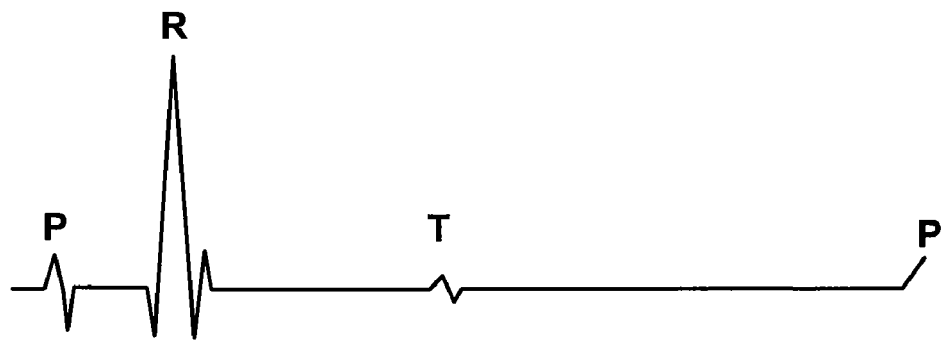
FIG. 3A illustrates a portion of an exemplary EGM signal.
Figure 3B:
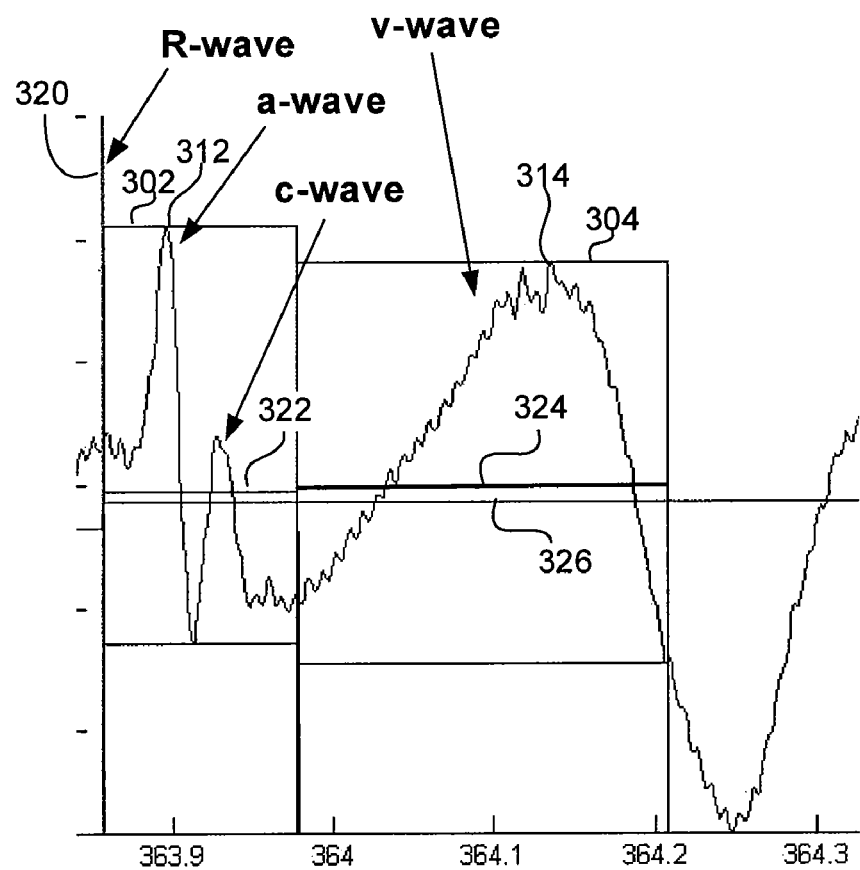
FIG. 3B illustrates an exemplary pressure signal representative of pressure within the left atrium a patient's heart, where the pressure signal corresponds to the EGM signal of FIG. 3A.

FIG. 3A illustrates a portion of an exemplary EGM signal, and FIG. 3B illustrates an exemplary corresponding pressure signal representative of pressure within the left atrium of a patient's heart. The signal of FIG. 3A can be obtained, e.g., by the implantable device 100, or a similar implantable device. The signal of FIG. 3B can be obtained, e.g., using the pressure sensor 145 that is attached by lead 103 to the implantable device 100.

Referring to FIG. 3A, each cycle of the EGM waveform, which corresponds to a heart beat, includes a P-wave that is a normally small positive wave caused by the beginning of a heart beat and representing atrial depolarization (also known as atrial activation), which initiates contraction of the atrial musculature. Following the P-wave there is a portion which is substantially constant in amplitude. The R-wave (representing ventricular depolarization, also known as ventricular activation) of the EGM is a rapid positive deflection that occurs after the substantially constant portion.

Referring to FIG. 3B, each cycle of the left atrial pressure waveform includes an a-wave, which is produced by an atrial contraction. Following the a-wave is a c-wave, which is produced by the left ventricle contracting against the closed mitral valve (MV). Following the c-wave is a v-wave, which is produced by the left ventricle end systole between the aortic valve closure and the mitral valve opening. Also shown in FIG. 3B are windows 302 and 304, which are discussed in more detail below during the discussion of FIG. 4. A vertical line 320 is representative of the relative timing of an R-wave, as detected from a corresponding EGM signal (e.g., as shown in FIG. 3A). Also shown are horizontal lines 322, 324 and 326, which are discussed in more detail below during the discussion of FIG. 4.

Figure 3C:
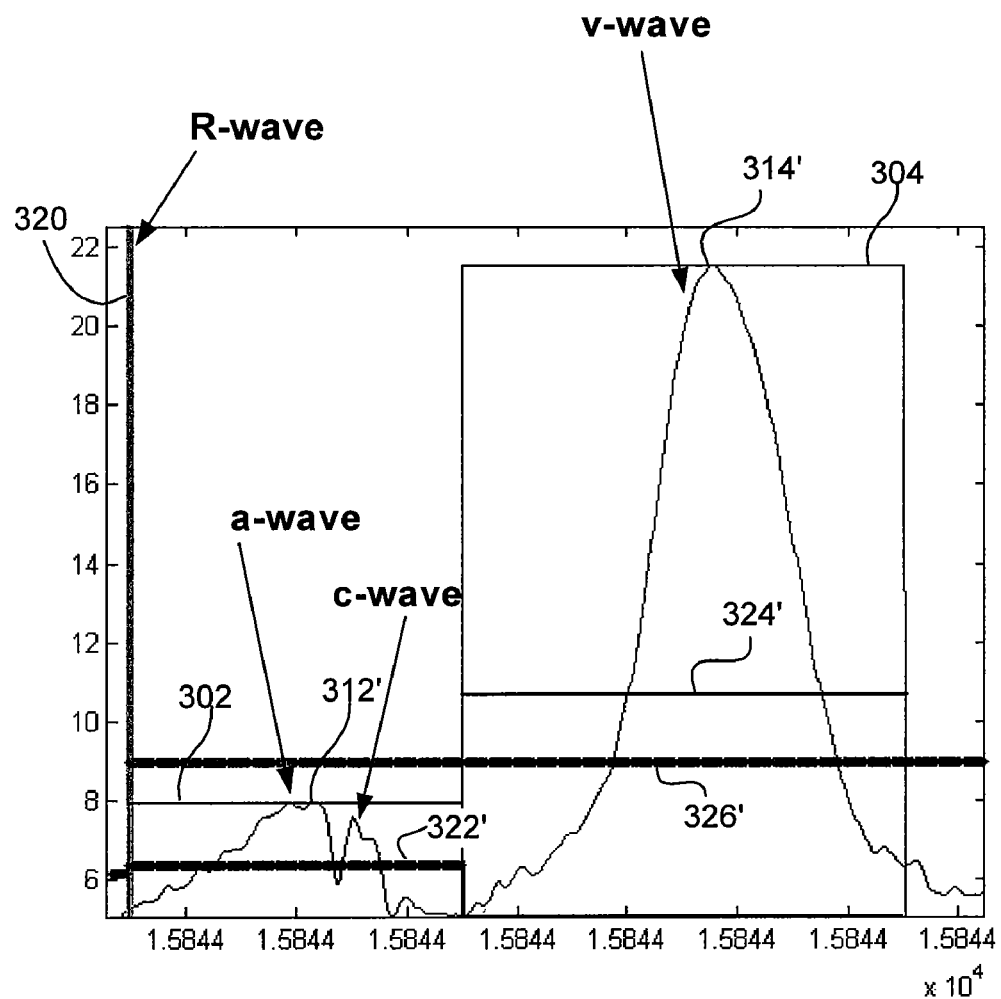
FIG. 3C illustrates an exemplary pressure signal representative of pressure within the left atrium a patient's heart, when the patient is experiencing MR.

Additional details of specific embodiments of the present invention will now be described with reference to the high level flow diagrams of FIGS. 4-6. During discussion of these flow diagram, frequent reference will be made back to the waveform of FIG. 3B. Reference will also be made to FIG. 3C, which is another left atrial pressure waveform.

Estimating Mean LAP

Figure 4:
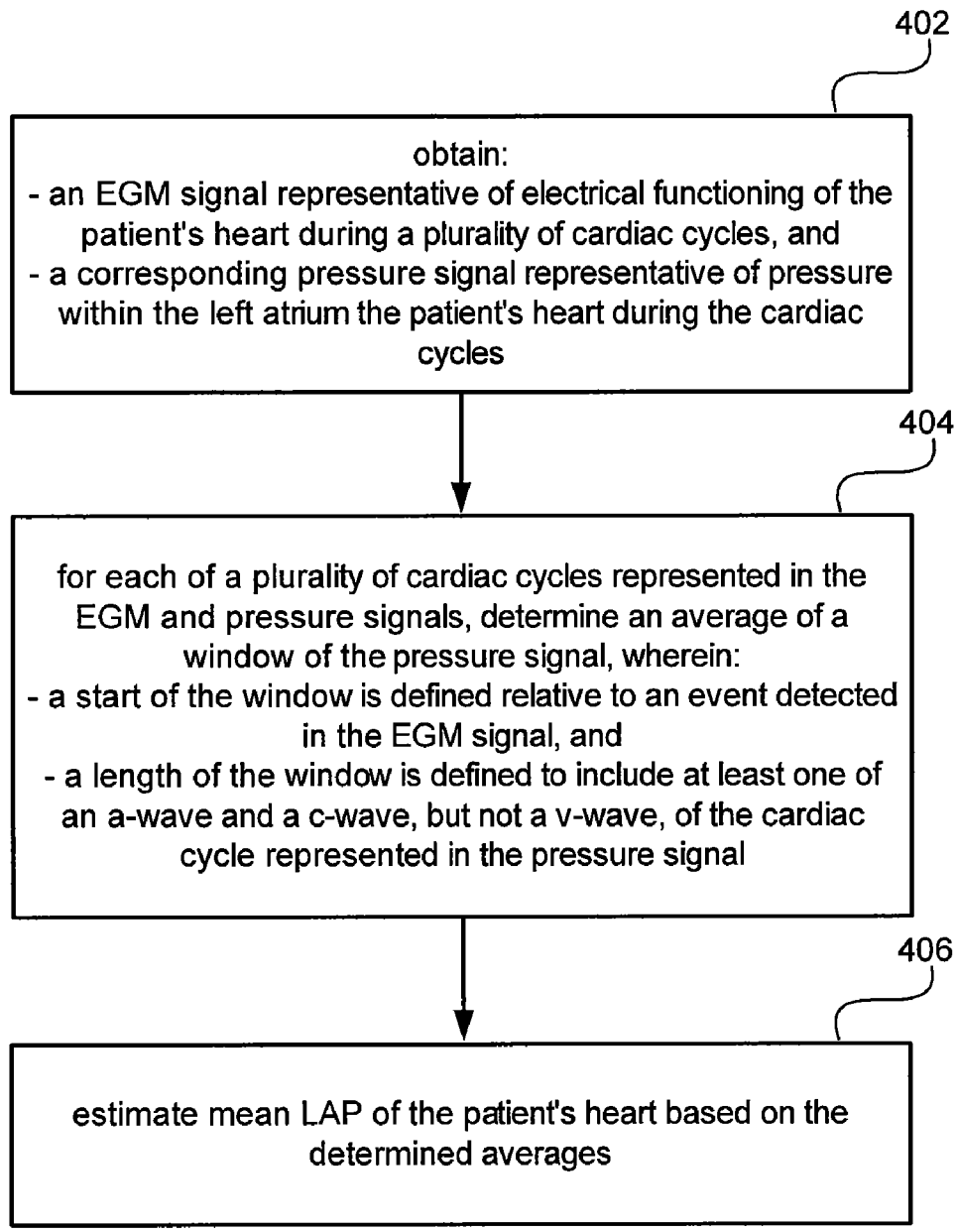
FIG. 4 is a high level flow diagram that is useful for describing how measures of mean left atrial pressure (LAP) can be estimated, in accordance with embodiments of the present invention.

FIG. 4 will now be used to describe how mean LAP can be estimated, in according with embodiments of the present invention. Referring to FIG. 4, at a step 402 an EGM signal and a corresponding pressure signal are obtained. The EGM signal is representative of electrical functioning of the patient's heart during a plurality of cardiac cycles, and the corresponding pressure signal is representative of pressure within the left atrium the patient's heart during the cardiac cycles.

At a step 404, for each of a plurality of cardiac cycles represented in the pressure signal there is a determination of an average (i.e., mean) of a window of the pressure signal. In accordance with specific embodiments, the start of the window is defined relative to an event detected in the EGM signal that corresponds to the pressure signal. In accordance with specific embodiments, the window is defined relative to a ventricular activation that is detected in the EGM signal. For example, referring to FIG. 3B, the vertical line 320 shows the timing of an R-wave, as detected from the EGM signal (of FIG. 3A) that corresponds to the pressure signal of FIG. 3B. Also shown in FIG. 3B is an exemplary window 302 that is defined relative to the R-wave represented by line 320. As was explained above, the R-wave is representative of an intrinsic ventricular activation. It is also possible that the ventricular activation is a paced V-pulse, instead of an intrinsic R-wave.

In this example, the start of the window 302 coincides with the ventricular activation, as detected based on a detected R-wave or V-pulse. However, this is not necessary. For example, the window may start a fixed delay after an R-wave or V-pulse. It is also possible that the window can be defined relative to an atrial activation (represented by a P-wave). Namely, if a device senses off the P-wave and knows the PR interval or AV delay, or has a good estimation of that value, the window can start a specified delay after a P-wave.

The length of each window (e.g., 302) is defined to include at least one of an a-wave and a c-wave, but not a v-wave, of the cardiac cycle represented in the pressure signal. Preferably, the length of the window is defined to include both the a-wave and the c-wave, as is the case with exemplary window 302 shown in FIG. 3B. In accordance with various embodiments, each window length may be a percentage of the previous or upcoming cardiac cycle length (e.g. 30%), or a percentage of the mean of a previous plurality of cardiac cycle lengths (e.g. 30% of the mean of the previous 8 RR intervals), or the length may be a fixed value (e.g. 120 ms). Mechanistically, the window preferably corresponds to the time after ventricular depolarization (i.e., activation) to the time of ventricular contraction and mitral valve closure. In terms of the LAP characteristics, this includes the "a-wave" and "c-wave" portions, as mentioned above.

Referring again to FIG. 4, at a step 406, the mean left atrial pressure (LAP) is estimated based on the averages determined at step 404. For example, each average determined for a cardiac cycle at step 404 can be used as a separate estimate of mean LAP. Alternatively, at step 406 an average can be determined of a plurality of the averages determined at step 404, and the average of the plurality of averages can be used as the estimate of mean LAP. In an alternative embodiment, at step 406 there is a determination of a median of a plurality of averages determined at step 404, and the median of the plurality of averages is used as the estimate of mean LAP.

An advantage of the embodiments described with reference to FIG. 4 is that they avoid the confounding effects of MR and conduction aberrances which result in large "v-waves" that occur in the LAP waveform late in the cardiac cycle. In other words, a large v-wave that may occur due to MR (as shown in FIG. 3C) will not corrupt the estimates of mean LAP, since the embodiments described above purposefully avoid measures of the v-wave when estimating mean LAP.

A response can be triggered when the estimated mean LAP exceeds a first threshold, or drops below a second threshold. Changes in mean LAP can also be monitored by repeatedly (e.g., continually, or from time to time) performing the steps discussed with reference to FIG. 4. In this manner, trends in the mean LAP of the patient can be monitored. Additionally, a response can be triggered if the change in mean LAP, within a specified amount of time, that exceeds a corresponding threshold.

Referring back to FIG. 2, the patient alert 221 can be used to inform a patient when their mean LAP exceeds a threshold or drops below a threshold. The device 100 can alternatively use the telemetry circuit to inform a physician, clinician and/or any other person (or processor) of the same. The patient alert 221 can include an indicator that provides, for example, an acoustic, mechanical vibration, optical and/or electrical indication and/or stimulation. Triggering of an alert can indicate to a patient, physician, clinician, monitoring staff, and/or monitoring computer, e.g., that a change in mean LAP that is indicative of a heart failure exacerbation (also known as, an episode of acute heart failure) is developing. The patient can be instructed to call his physician when the patient alert is triggered, and/or the patient can be instructed to take a specific drug (e.g., a diuretic) when the patient alert is triggered. It is also possible that the implantable device includes a drug pump (e.g., 261) that will deliver an appropriate dosage of a drug (e.g., a diuretic) in response to one or more of the conditions mentioned above (e.g., estimated mean LAP exceeds a first threshold, or drops below a second threshold). In accordance with an embodiment of the present invention, mean LAP information can be stored. This can include, for example, storing mean LAP estimates (which can be displayed with previously determined mean LAP estimates, from a month ago, and compared to see improvement or worsening CHF condition). Such information can be continually, or from time to time, automatically uploaded to an external device (e.g., 254). Such an external monitoring device can be located, e.g., in the patients' home, and the information can be transmitted (e.g., through telephone lines or the Internet) to a medical facility where a physician can analyze the information. Alternatively, the external device can be located at a medical facility, and the information can be uploaded when the patient visits the facility.

A threshold can be predetermined. Alternatively, a threshold can be dynamic in that its value is determined based on previously measured and/or calculated values. A common threshold can be used for many patients. Alternatively, thresholds can be patient specific.

Monitoring for Mitral Valve Regurgitation (MR)

Figure 5:
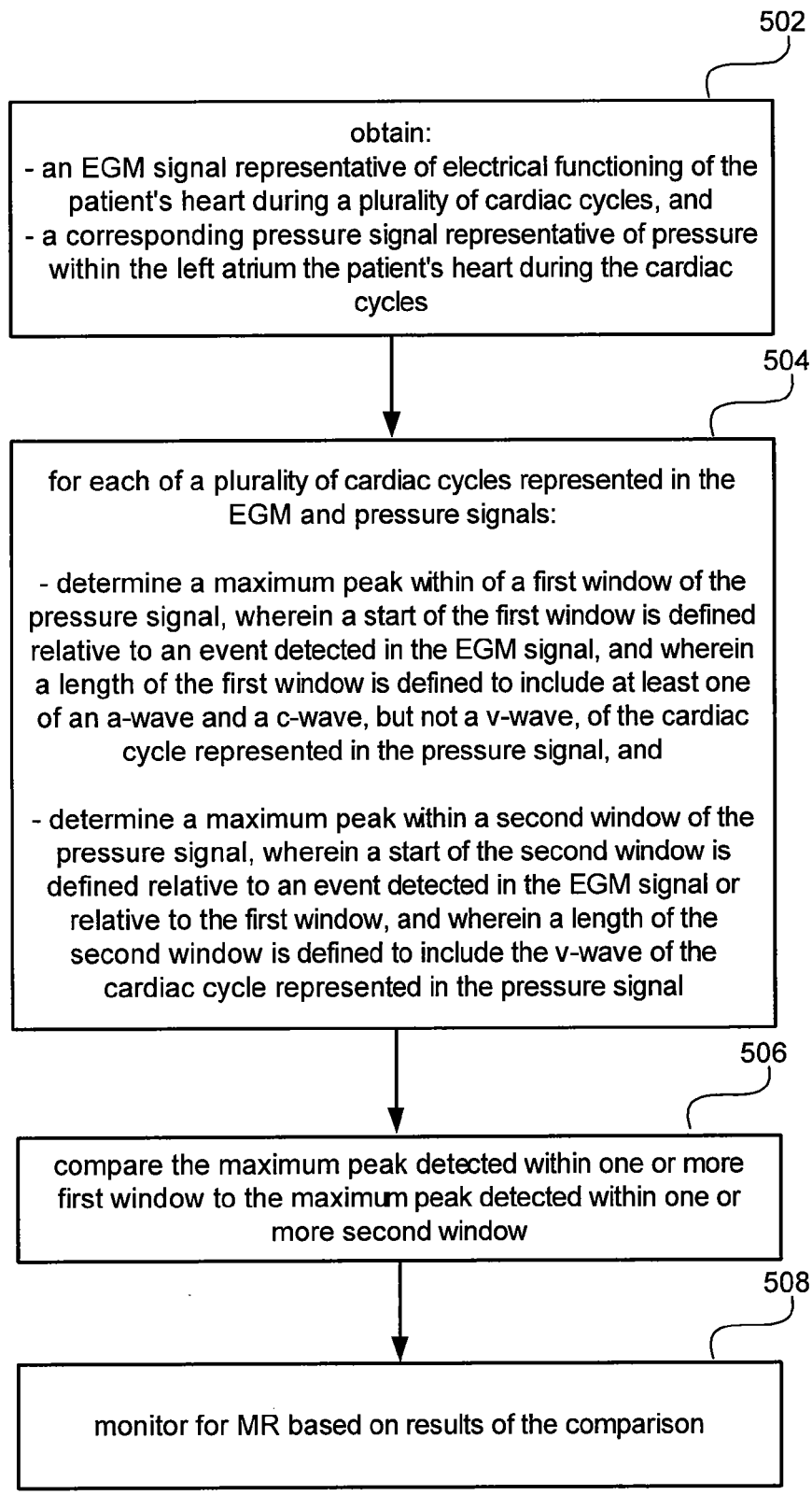
FIG. 5 is a high level flow diagram that is useful for describing how to monitor for MR, in accordance with embodiments of the present invention.

FIG. 5 will now be used to describe how to monitor for MR, in according with embodiments of the present invention. Referring to FIG. 5, at a step 502, which is similar to step 402, an EGM signal and a corresponding pressure signal are obtained. The EGM signal is representative of electrical functioning of the patient's heart during a plurality of cardiac cycles, and the corresponding pressure signal is representative of pressure within the left atrium the patient's heart during the cardiac cycles.

At a step 504, for each of a plurality of cardiac cycles represented in the EGM and pressure signals, there is a determination of a maximum peak within a first window of the pressure signal, and a determination of a maximum peak within a second window of the pressure signal. The first window is defined to include at least one of an a-wave and a c-wave, but not a v-wave, of the cardiac cycle represented in the pressure signal. The second window is defined to include the v-wave of the cardiac cycle represented in the pressure signal. For the embodiments described with reference to FIG. 5, it is preferred that the second window includes neither the a-wave or the c-wave.

In accordance with specific embodiments, the start of the first window is defined relative to an event detected in the EGM signal, in any of the manners as was discussed above with regards to step 404 of FIG. 4. Referring to FIG. 3B, the window 302 is an example of such a first window. The start of the second window can be defined relative to an event in the EGM, or relative to the first window. Referring to FIG. 3B, the window 304 is an example of such a second window. The second window 304 can be defined as starting at the end of the first window, e.g., as shown in FIG. 3B. Alternatively, the second window 304 can be defined as starting a specified delay after a ventricular or atrial activation. For example, the second window can be defined to start 120 msec after a ventricular activation. It is also possible that there can be a small time gap between the first and second windows, or a small overlap between first and second windows, although such gap or overlap is not preferred.

The length of each second window may be a percentage of the previous or upcoming cardiac cycle length (e.g. 70%), or a percentage of the mean of a previous plurality of cardiac cycle lengths (e.g. 70% of the mean of the previous 8 RR or W intervals), or the length may be a fixed value (e.g. 280 ms). It may also be that the length of the second window is the remainder of a cycle length not included in the first window. Mechanistically, the second window preferably corresponds to the time after ventricular contraction and mitral valve closure to the time of the next ventricular activation.

Referring again to FIG. 5, at a step 506 the maximum peak detected within one or more first window is compared to a maximum peak detected within one or more second window. For example, the peaks of the first and second windows for each cardiac cycle can be compared to one another at step 506. Alternatively, at step 506 an average (or median) can be determined of a plurality of first window peaks determined at step 504, and an average (or median) can be determined of a plurality of second window peaks determined at step 504, and then the average (or median) first window peak can be compared to the average (or median) second window peak.

Still referring to FIG. 5, at a step 508, MR is monitored for based on results of the comparison(s) performed at step 506. Reference back to FIG. 3B shows that the peak 314 within the second window 302 is about the same as the peak 312 within the first window 302. This is indicative of an absence of MR. In contrast, FIG. 3C shows that the peak 314' within the second window 304 is much greater than the peak 312' within the first window 302, which is indicative of the presence of MR.

Step 508 can be accomplished in a variety of manners. For example, step 508 can include determining a ratio based on the maximum peak detected within one or more first window to the maximum peak detected within one or more said second window, (or vice versa), and detecting MR when the ratio falls below (or exceeds) a corresponding threshold. Alternatively, step 508 can include determining a difference between the maximum peak detected within one or more first window and the maximum peak detected within one or more second window, and detecting MR when the difference exceeds a corresponding threshold.

Figure 6:
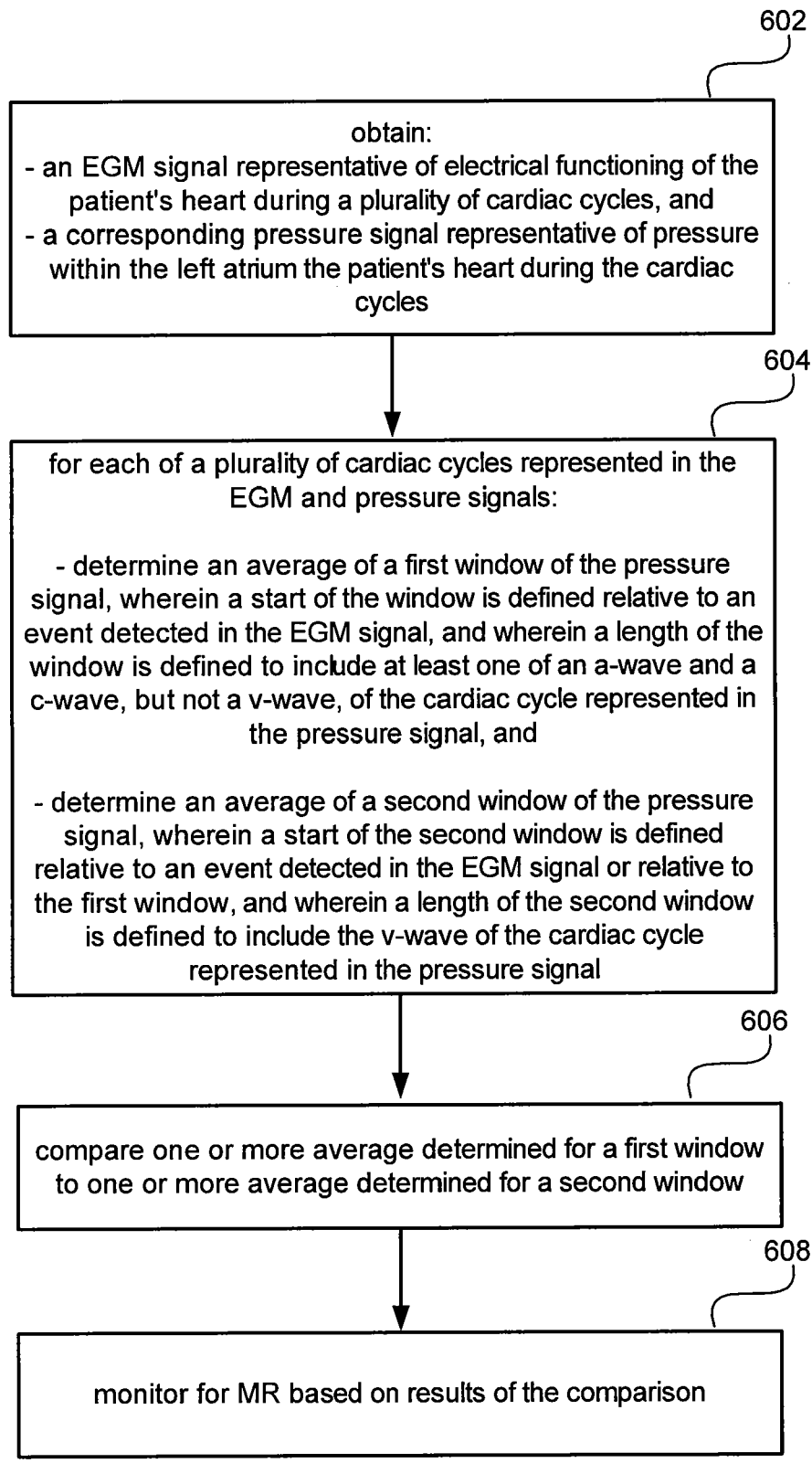
FIG. 6 is a high level flow diagram that is useful for describing how to monitor for MR, in accordance with alternative embodiments of the present invention.

FIG. 6 will now be used to describe how to monitor for MR, in according with other embodiments of the present invention. Referring to FIG. 6, at a step 602, which is similar to steps 402 and 502, an EGM signal and a corresponding pressure signal are obtained, where the EGM signal is representative of electrical functioning of the patient's heart during a plurality of cardiac cycles, and the corresponding pressure signal is representative of pressure within the left atrium the patient's heart during the cardiac cycles.

At a step 604, for each of a plurality of cardiac cycles represented in the EGM and pressure signals, there is a determination of an average of a first window of the pressure signal, and a determination of an average of a second window of the pressure signal. The first window is defined to include at least one of an a-wave and a c-wave, but not a v-wave, of the cardiac cycle represented in the pressure signal. The second window is defined to include the v-wave of the cardiac cycle represented in the pressure signal. The start and length of the first window can be defined in the same manners that the first window can be defined with reference to step 504.

In the embodiments discussed with reference to FIG. 6, the start of the second window can be defined relative to an event in the EGM, or relative to the first window. Referring to FIG. 3B, the window 304 is an example of such a second window. The second window 304 can be defined as starting at the end of the first window. Alternatively, the second window 304 can be defined as starting a specified delay after a ventricular or atrial activation. For example, the second window can be defined to start 120 msec after a ventricular activation. It is also possible that there is a small time gap between the first and second windows, or a small overlap between the first and second windows. In this embodiments discussed with reference to FIG. 6 is also possible that the second window encompass an entire cardiac cycle (e.g., RR or VV interval), and thus that the second window completely encompasses the first window. For example, it is possible that the second window starts where the first window starts, but that the second window is longer than the first window so that the second window will include the v-wave.

At a step 606, one or more average determined for a first window is compared to one or more average determined for a second window. For example, the average of the first window and the average of the second window for each cardiac cycle can be compared to one another at step 606. Alternatively, at step 606 an average (or median) can be determined of a plurality of first window averages determined at step 604, and an average (or median) can be determined of a plurality of second window averages determined at step 404, and then the average (or median) first window average can be compared to the average (or median) second window average. It is noted that where the length of the second window is equal to an entire cardiac cycle, the average determined for the second window is an average of an entire cardiac interval represented in the left atrial pressure signal.

Still referring to FIG. 6, at a step 608 MR is monitored for based on results of the comparison(s) performed at step 606. Referring back to FIG. 3B, an exemplary first window is shown at 302, and an exemplary second window is shown at 304, with horizontal line 322 illustrating the average of the first window 302, and horizontal line 324 illustrating the average of the second window 304. It can be appreciated that the average 324 of the second window 304 is about the same as the average 322 of the first window 302. This is indicative of an absence of MR. In contrast, referring to FIG. 3C, it can be appreciated that the average 324' of the second window 304 is significantly greater than the average 322' of the first window 302, which is indicative of the presence of MR.

As mentioned above, it is also possible that the length of the second window is equal to an entire cardiac cycle. In such a case, the average determined for the second window is the average of the entire cardiac interval represented in the left atrial pressure signal, which is illustrated by line 326 in FIG. 3B, and by line 326' in FIG. 3C. It can be appreciated from FIG. 3B that the average 326 of the second window (where the second window extends an entire cardiac interval) is about the same as the average 322 of the first window 302, which is indicative of an absence of MR. It can be appreciated from FIG. 3C that the average 326' of the second window (where the second window extends an entire cardiac interval) is significantly greater than the average 322' of the first window 302, which is indicative of the presence of MR.

Step 608 can be accomplished in a variety of manners. For example, step 608 can include determining a ratio based on the average of one or more first window to the average of one or more second window, (or vice versa), and detecting MR when the ratio falls below (or exceeds) a corresponding threshold. Alternatively, step 608 can include determining a difference between the average of one or more first window and the average of one or more second window, and detecting MR when the difference exceeds a corresponding threshold.

One or more response can be triggered if MR is detected. In accordance with an embodiment of the present invention, information related to each MR can be stored. This can include, for example, storing pressure signal data for each MR and/or providing a measure of MR burden (which can be displayed with previously determined MR burdens, from a month ago, and compared to see improvement or worsening of MR condition). Such information can be continually, or from time to time, automatically uploaded to an external device (e.g., 254). Such an external monitoring device can be located, e.g., in the patients' home, and the information can be transmitted (e.g., through telephone lines or the Internet) to a medical facility where a physician can analyze the information. Alternatively, the external device can be located at a medical facility, and the information can be uploaded when the patient visits the facility.

Figure 7:
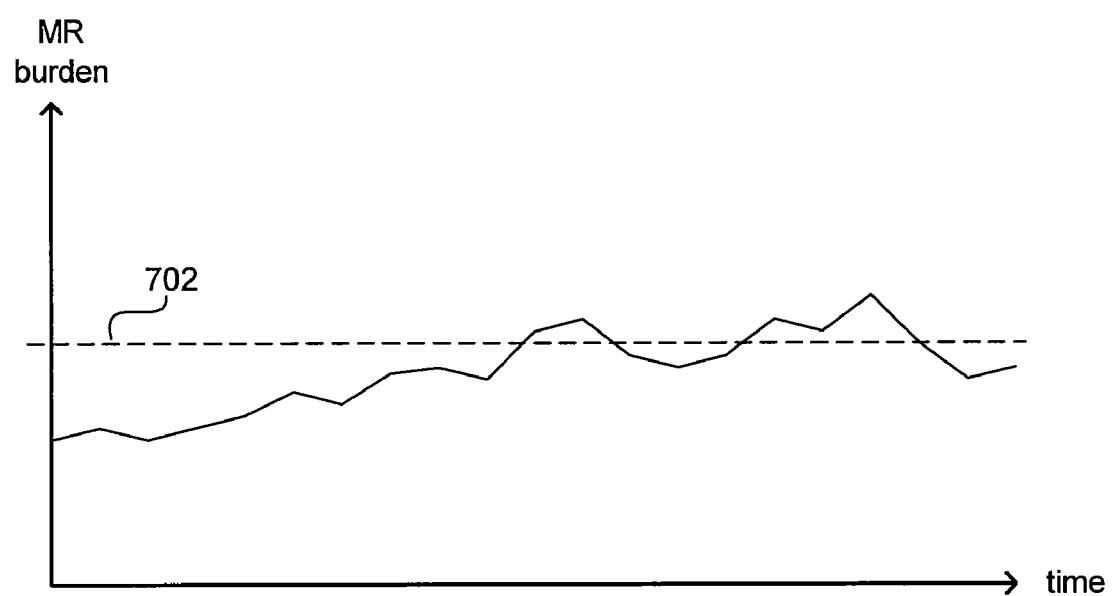
FIG. 7 is an exemplary graph of MR burden versus time that can be produced using embodiments of the present invention.

In accordance with an embodiment of the present invention, MR burden can be monitored by determining a number of MRs that occur during each predetermined period of time (e.g., 24 hours). By tracking MR burden in this manner, there can be a determination of whether MR burden has increased or decreased over time. Additionally, one or more MR burden threshold can be defined, so that one of the above responses can be triggered in response to a specific MR burden threshold being crossed. FIG. 7 shows an exemplary graph of MR burden over time, with dashed line 702 representing an exemplary threshold.

Example embodiments of the methods, systems, and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein.

Thus, the breadth and scope of the present invention should not be limited by any of the above-described exemplary embodiments, but should be defined only in accordance with the following claims and their equivalents.

What is claimed is:

1. In an implantable system, a method for monitoring a patient's heart for mitral valve regurgitation (MR), comprising:
   (a) obtaining an electrogram (EGM) signal and a corresponding pressure signal, the EGM signal representative of electrical functioning of the patient's heart during a plurality of cardiac cycles, the corresponding pressure signal representative of pressure within the left atrium the patient's heart during the cardiac cycles;
   (b) for each of a plurality of cardiac cycles represented in the EGM and pressure signals,
      (b.1) determining a maximum peak within a first window of the pressure signal,
         wherein a start of the first window is defined relative to an event detected in the EGM signal, and
         wherein a length of the first window is defined to include at least one of an a-wave and a c-wave, but not a v-wave, of the cardiac cycle represented in the pressure signal; and
      (b.2) determining a maximum peak within a second window of the pressure signal,
         wherein a start of the second window is defined relative to an event detected in the EGM signal or relative to the first window, and
         wherein a length of the second window is defined to include the v-wave of the cardiac cycle represented in the pressure signal;
   (c) comparing the maximum peak detected within one or more said first window to the maximum peak detected within one or more said second window; and
   (d) monitoring for MR based on results of the comparing.

2. The method of claim 1, wherein:
   step (c) includes determining a ratio based on the maximum peak detected within one or more said first window and the maximum peak detected within one or more said second window, or vice versa; and
   step (d) includes detecting MR by comparing the ratio to a threshold.

3. The method of claim 1, wherein:
   step (c) includes determining a difference between the maximum peak detected within one or more said first window and the maximum peak detected within one or more said second window; and
   step (d) includes detecting MR when the difference exceeds a threshold.

4. An implantable system for monitoring a patient's heart for mitral valve regurgitation (MR), comprising:

one or more electrode to obtain an electrogram (EGM) signal representative of electrical functioning of the patient's heart during a plurality of cardiac cycles;

one or more sensor to obtain a corresponding pressure signal representative of pressure within the left atrium the patient's heart during the cardiac cycles; and one or more processor to determine, for each of a plurality of cardiac cycles represented in the EGM and pressure signals, a maximum peak within of a first window of the pressure signal, wherein a start of the first window is defined relative to an event detected in the EGM signal, and wherein a length of the first window is defined to include at least one of an a-wave and a c-wave, but not a v-wave, of the cardiac cycle represented in the pressure signal; and a maximum peak within a second window of the pressure signal, wherein a start of the second window is defined relative to an event detected in the EGM signal or relative to the first window, and wherein a length of the second window is defined to include the v-wave of the cardiac cycle represented in the pressure signal;

wherein the one or more processor monitors for MR based on comparisons of the maximum peak detected within one or more said first window to the maximum peak detected within one or more said second window.

5. The system of claim 4, wherein the one or more processor:

determines a ratio based on the maximum peak detected within one or more said first window and the maximum peak detected within one or more said second window, or vice versa; and detects MR by comparing the ratio to a threshold.

6. The system of claim 4, wherein the one or more processor:

determines a difference between the maximum peak detected within one or more said first window and the maximum peak detected within one or more said second window; and detects MR when the difference exceeds a threshold.

* * * * *